United States Patent
Perez et al.

(10) Patent No.: US 10,460,077 B2
(45) Date of Patent: Oct. 29, 2019

(54) SECURELY COLLECTING AND PROCESSING MEDICAL IMAGERY

(71) Applicant: GreatDef Corp., Solana Beach, CA (US)

(72) Inventors: Marc Perez, San Marcos, CA (US); Michael O'Leary, Solana Beach, CA (US)

(*) Notice: Subject to any disclaimer, the term of this patent is extended or adjusted under 35 U.S.C. 154(b) by 0 days.

(21) Appl. No.: 15/485,209

(22) Filed: Apr. 11, 2017

(65) Prior Publication Data
US 2017/0293718 A1   Oct. 12, 2017

Related U.S. Application Data

(63) Continuation-in-part of application No. 15/336,781, filed on Oct. 27, 2016.
(Continued)

(51) Int. Cl.
*G06F 19/00*  (2018.01)
*G06F 21/79*  (2013.01)
(Continued)

(52) U.S. Cl.
CPC ........ *G06F 19/321* (2013.01); *G06F 21/6209* (2013.01); *G06F 21/79* (2013.01); *G16H 10/65* (2018.01); *G06Q 2220/00* (2013.01)

(58) Field of Classification Search
CPC ...... G06F 19/321; G06F 19/323; G06F 21/79; G06K 9/00892; G06Q 2220/00; G06T 1/20
See application file for complete search history.

(56) References Cited

U.S. PATENT DOCUMENTS

| | | | | |
|---|---|---|---|---|
| 5,892,825 A | * | 4/1999 | Mages | G06F 21/10 380/277 |
| 5,937,164 A | * | 8/1999 | Mages | G06F 21/10 375/E7.025 |

(Continued)

FOREIGN PATENT DOCUMENTS

| | | | |
|---|---|---|---|
| CN | 108985078 A | * 12/2018 | |
| WO | WO 2015154069 A1 | * 10/2015 | ............. G06T 19/20 |

OTHER PUBLICATIONS

"Wikipedia"m IEEE802.1X is an IEEE Standard for port-based Network Access Control (PNAC).pp. 1-8, see. IEEE 802.1X-2001.*

*Primary Examiner* — Mekonen T Bekele
(74) *Attorney, Agent, or Firm* — Zion Maffeo

(57) ABSTRACT

A system for recording HIPAA compliant medical imagery may be configured using two separate systems. A first system comprising a separate and independent medical imaging device such as a microscope, an endoscope, or a similar medical imaging tool. The desired medical imaging tool is configured so that a high-definition recording device is able to capture the imagery displayed by the medical imaging tool. The separate and independent medical imaging device is further configured to transmit the high-definition captured imagery to a second separate and independent medical imagery processing system. The second separate and independent medical imagery processing system may be configured to include a special purpose computer with a processor, a hard drive, a random-access memory, and a removable encrypted flash drive. The processor may be configured, using well understood techniques, to process the high-definition imagery that is transmitted from the separate and independent medical imaging device. The processor may be further configured to store the processed data in an encrypted format only on a removable encrypted flash drive (Continued)

that is connected to the second separate and independent medical imagery processing system.

20 Claims, 4 Drawing Sheets

Related U.S. Application Data

(60) Provisional application No. 62/321,723, filed on Apr. 12, 2016.

(51) Int. Cl.
*G16H 10/65* (2018.01)
*G06F 21/62* (2013.01)

(56) References Cited

U.S. PATENT DOCUMENTS

| | | | | |
|---|---|---|---|---|
| 6,424,574 B1* | 7/2002 | Chou | ............. | G11C 16/344 365/185.29 |
| 9,336,402 B2* | 5/2016 | Wong | ............. | G06F 21/62 |
| 2003/0227673 A1* | 12/2003 | Nakagawa | ............. | G02B 21/241 359/380 |
| 2008/0219453 A1* | 9/2008 | Chang | ............. | H04L 9/0897 380/286 |
| 2008/0243550 A1* | 10/2008 | Yao | ............. | G06Q 50/24 705/3 |
| 2009/0076849 A1* | 3/2009 | Diller | ............. | G06F 21/6245 705/3 |
| 2009/0183008 A1* | 7/2009 | Jobmann | ............. | H04L 9/0866 713/186 |
| 2009/0276223 A1* | 11/2009 | Jaiswal | ............. | G10L 15/26 704/270.1 |
| 2010/0054476 A1* | 3/2010 | Schneider | ............. | H04L 9/0894 380/277 |
| 2011/0135171 A1* | 6/2011 | Galigekere | ............. | G06T 7/0012 382/128 |
| 2011/0164314 A1* | 7/2011 | Shirota | ............. | G02B 21/365 359/387 |
| 2011/0258411 A1* | 10/2011 | Sato | ............. | G06F 3/0623 711/165 |
| 2012/0002033 A1* | 1/2012 | Yamane | ............. | G02B 21/365 348/79 |
| 2012/0131336 A1* | 5/2012 | Price | ............. | G06F 21/78 713/165 |
| 2012/0162401 A1* | 6/2012 | Melder | ............. | H04N 7/183 348/65 |
| 2013/0022268 A1* | 1/2013 | Kishima | ............. | G06T 5/002 382/173 |
| 2013/0167228 A1* | 6/2013 | Wong | ............. | G06F 21/62 726/19 |
| 2013/0191647 A1* | 7/2013 | Ferrara, Jr. | ............. | G06F 21/32 713/186 |
| 2013/0247222 A1* | 9/2013 | Maksim | ............. | G06F 21/6218 726/28 |
| 2015/0019875 A1* | 1/2015 | Barbiero | ............. | G06F 21/602 713/189 |
| 2015/0127316 A1* | 5/2015 | Avisar | ............. | G06T 13/20 703/11 |
| 2015/0180536 A1* | 6/2015 | Zhang | ............. | H04B 3/23 381/66 |
| 2015/0304322 A1* | 10/2015 | Zaidi | ............. | G06K 9/00892 382/115 |
| 2016/0117519 A1* | 4/2016 | Hashii | ............. | G06F 21/6218 713/166 |
| 2017/0035517 A1* | 2/2017 | Geri | ............. | G06T 19/20 |

* cited by examiner

SECURELY COLLECTING AND PROCESSING MEDICAL IMAGERY

CROSS REFERENCE TO RELATED APPLICATIONS

This application claims priority to U.S. Provisional Application No. 62/321,723 filed Apr. 12, 2016, and entitled "COLLECTING AND PROCESSING MEDICAL IMAGERY." This application also claims priority to U.S. Non-provisional application Ser. No. 15/336,781 filed Oct. 27, 2016. The content of this prior application is considered part of this application, and is hereby incorporated by reference in its entirety.

BACKGROUND

Field

The described technology generally relates to electronics and, more specifically, to secure medical image collection and processing.

Description of the Related Art

Medical imaging systems traditionally lack the ability to securely record and transmit data in an efficient manner. Additionally, high definition imagery is not available on current microscopy systems. This limits the adoption and efficacy of such important tools for the medical practice.

SUMMARY

The methods and devices of the described technology each have several aspects, no single one of which is solely responsible for its desirable attributes.

In one embodiment, a microscope system is configured to record events in high definition. The microscope system is further configured to transmit high definition video or images to a second system. The second system comprising a processor, memory, and one or more removable storage devices. The second system further comprising video capture software configured to process and store the high definition video or images and one or more mobile devices configured to display the high definition video or images.

BRIEF DESCRIPTION OF THE DRAWINGS

These drawings and the associated description herein are provided to illustrate specific embodiments of this disclosure and are not intended to be limiting. The above-mentioned aspects, as well as other features, aspects, and advantages of the present technology will now be described in connection with various implementations, with reference to the accompanying drawings. Throughout the drawings, similar symbols typically identify similar components, unless context dictates otherwise. Note that the relative dimensions of the following figures may not be drawn to scale.

DETAILED DESCRIPTION

Various aspects of the novel systems, apparatuses, and methods are described more fully hereinafter with reference to the accompanying drawings. Aspects of this disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the novel systems, apparatuses, and methods disclosed herein, whether implemented independently of or combined with any other aspect. For example, an apparatus may be implemented or a method may be practiced using any number of the aspects set forth herein. In addition, the scope is intended to encompass such an apparatus or method which is practiced using other structure, functionality, or structure and functionality in addition to or other than the various aspects set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to automotive systems and/or different wired and wireless technologies, system configurations, networks, including optical networks, hard disks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

Figure 1:
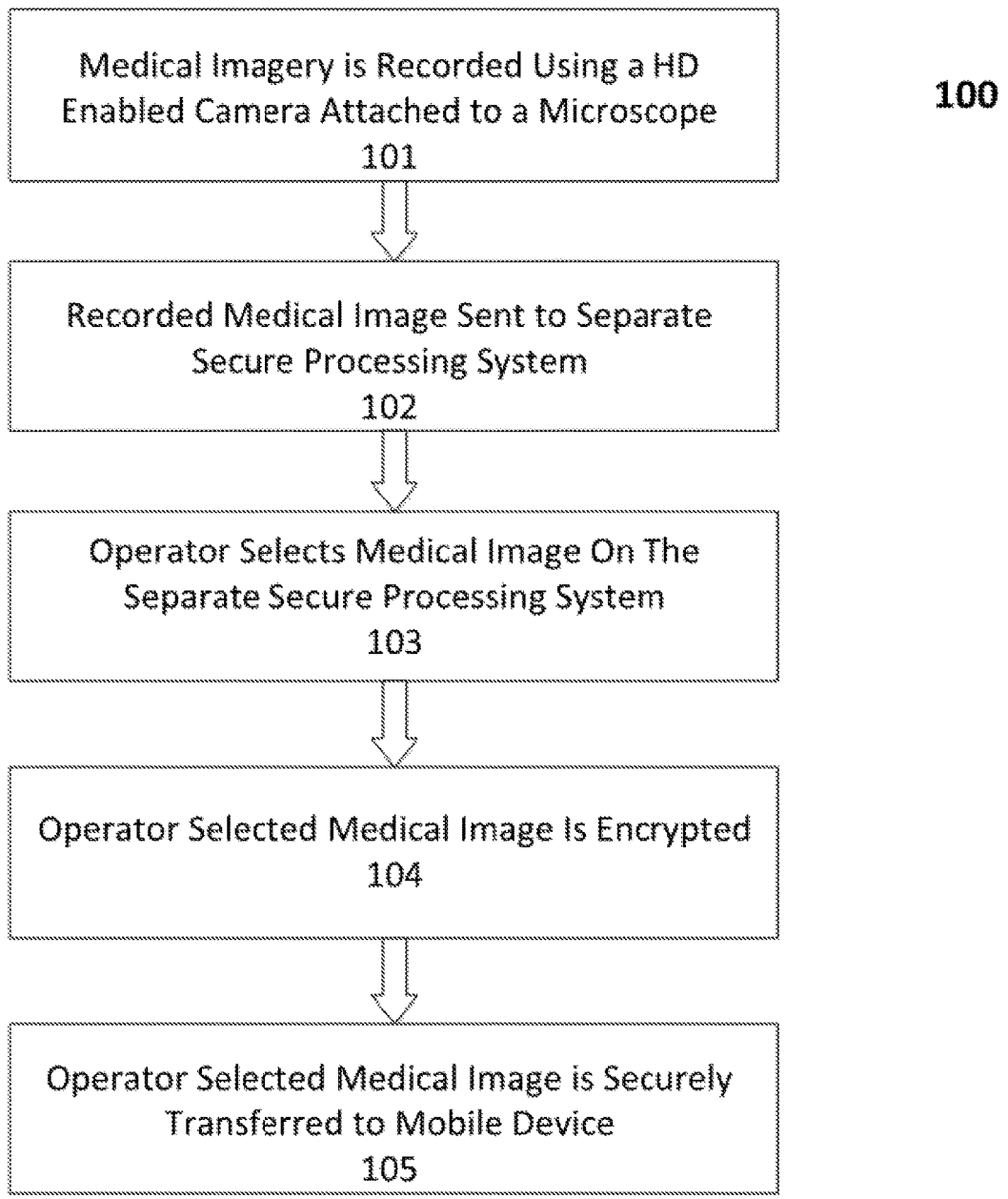
FIG. 1 is a flow chart illustrating an example digital image collection scheme according to one embodiment.

FIG. 1 exemplifies one embodiment of a process of capturing high definition video and/or imagery as further discussed below. An operator, who may be a medical professional such as a surgeon, general practitioner, nurse, aide, technician or otherwise qualified person may use a medical a HD enabled camera attached to a microscope to record medical imagery. It will be understood that it is not necessary to use a microscope and any medical imagery device fitted with a HD enabled camera may be used including a microscope, endoscope, sonogram, radiological imaging device, or other similar medical imaging technology. In one embodiment a microscope is configured with a high definition camera capable of capturing high definition video and/or imagery. High definition video is video that conforms to a standard of no less than 720p, 1080i and 1080p. Additional high definition standards which have high resolution are contemplated. According to another embodiment, the microscope may be configured with a high definition camera that attaches to an eyepiece of the microscope. In a further embodiment, the microscope may be present a shared display with high definition, low definition, and analog signals each available for use and recording by an operator. Many embodiments know to those skilled in the art are contemplated.

The recorded medical imagery The designated operator may be a qualified person as described above or the designee of the qualified person. The command to capture may be made by voice command, as disclosed in more detail below. In other embodiments, the command to capture may made by a remote wireless device such as a Bluetooth mouse, IR devise, wireless keyboard, or WiFi connected device. Further, the command to capture may be made be made by any one of a number of designated operators each of which may be authorized with the authority to direct the capture of one or more elements depending on their designated authority.

The command to capture of FIG. 1 may be directed to the capture of individual images, video imagery, audio imagery, 3D stereoscopic images or any combination of these. Images captured may be in jpeg, bmp, tiff, gif, or other digital imagery format. Video captured may be in mp4, HTML5, .avi, or other form known in the art. In some embodiments, the capture of this data may further be stored in an encrypted format in some embodiments. HIPAA and electronic medical record data standards may be implemented to optimize and secure the process by which data is captured. Where a HIPAA compliant encryption algorithm is required an algorithm selected from the Federal Information Processing Standards (FIPS) 140-2 Annex A or an equivalent is be used.

FIG. 1 further describes a process according to one embodiment where the data discussed above may be automatically transferred, processed, and stored by the system disclosed further herein. The data may be transferred to an electronic storage system such as a computer file system, database, removable storage or computer memory. The data is stored with an automatically generated filename, which may be changed by an authorized operator. In some embodiments the data may be associated with similar data selected by the operator to form a combined data set. By way of example, video imagery of a surgery may be electronically associated with a computer recording of a doctor's audio commentary.

In some embodiment's of the process set out in FIG. 1 the data is automatically transferred to a local storage device. In another embodiment the data is transferred to a remote device over a secure link. The remote device may be another system similar to the system described herein. According to other embodiments, the data may be transferred to a mobile device such as a laptop, tablet, or mobile device. In other embodiments, data is transferred to a remote network or a remote system over a secure connection that complies with HIPA standards. This remote network is a HIPA compliant system such as an EMR system or medical insurance associated system. In other embodiments, the transfer of data may be commenced upon the command of an authorized user.

Figure 2:
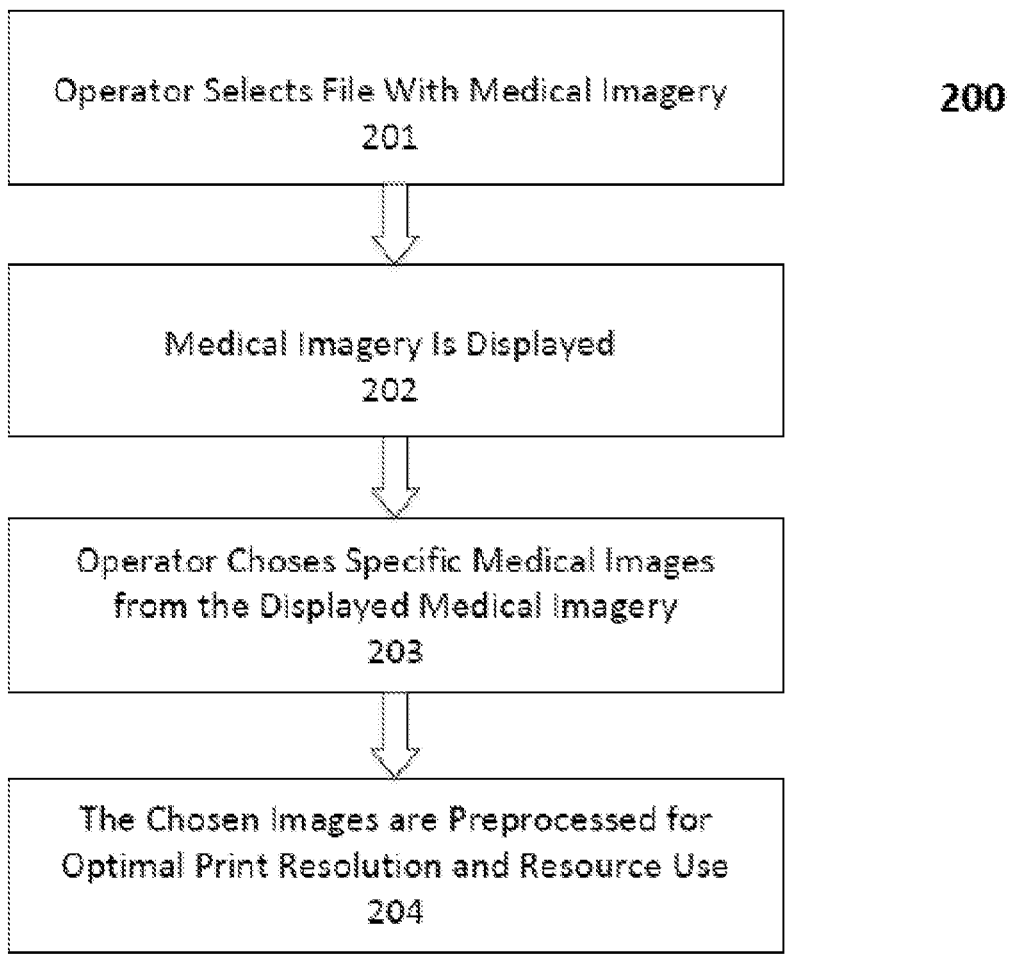
FIG. 2 is a flow chart showing an example process for digital image printing according to one embodiment.

FIG. 2 exemplifies one embodiment of a process to print physical pictures of the digital images and/or frames from digital videos as described in more detail herein. An operator selects a file with medical imagery 201. Medical imagery is displayed 202. The operator chooses specific medical images from the displayed medical imagery 203. The chosen images are preprocessed for optimal print resolution and resource use 204.

In some embodiments the operator is an authorized user who has accessed the system 200 shown in FIG. 2 by using personal credentials. The operator may select a file with medical imagery 201 using GUI application on a computer screen. The GUI is configured to operate computer code that opens the file and presents the authorized operator with a selection of medical imagery as described in step 202. These medical images in some embodiments are represented as thumbnails of digital images and/or video. In other embodiments these medical images may be combined rich data with audio, metadata, medical notes, and other data combined with a digital image or video in order to provide medically relevant information to those with access to that digital file. An operator may select one or more of the thumbnails. The user may then chose to add text that will be printed alongside the selected thumbnails.

As further presented in one embodiment of FIG. 2, an authorized user may select an option to print one or more of the selected thumbnails as described in step 203. In one embodiment of step 204 software code that optimizes the number of pages used to print the desired thumbnails and any associated text is then run. This software code uses well understood techniques to configure a printer to print in either landscape or portrait mode. Additionally, the software code may attempt to correlate a desired resolution selected by a user and the resolution capabilities of the printer used. This information is used to optimize the number of images printed on each sheet of paper. In a further embodiment, a user is prompted to input one or more of the inputs described above before a print command is accepted by the computer.

In some embodiments of FIG. 2, additional elements, drivers, sensors, chips, or modules, such as a memory storage device (random-access memory, read-only memory, flash memory, or solid state storage (SSD)), not expressly illustrated in FIG. 2. It is to be noted that all or parts of the steps in FIG. 2 may be concurrently, continuously, periodically, intermittently, repeatedly, or iteratively performed, and the illustrated process in FIG. 2 is only one example embodiment of the features disclosed herein.

Figure 3:
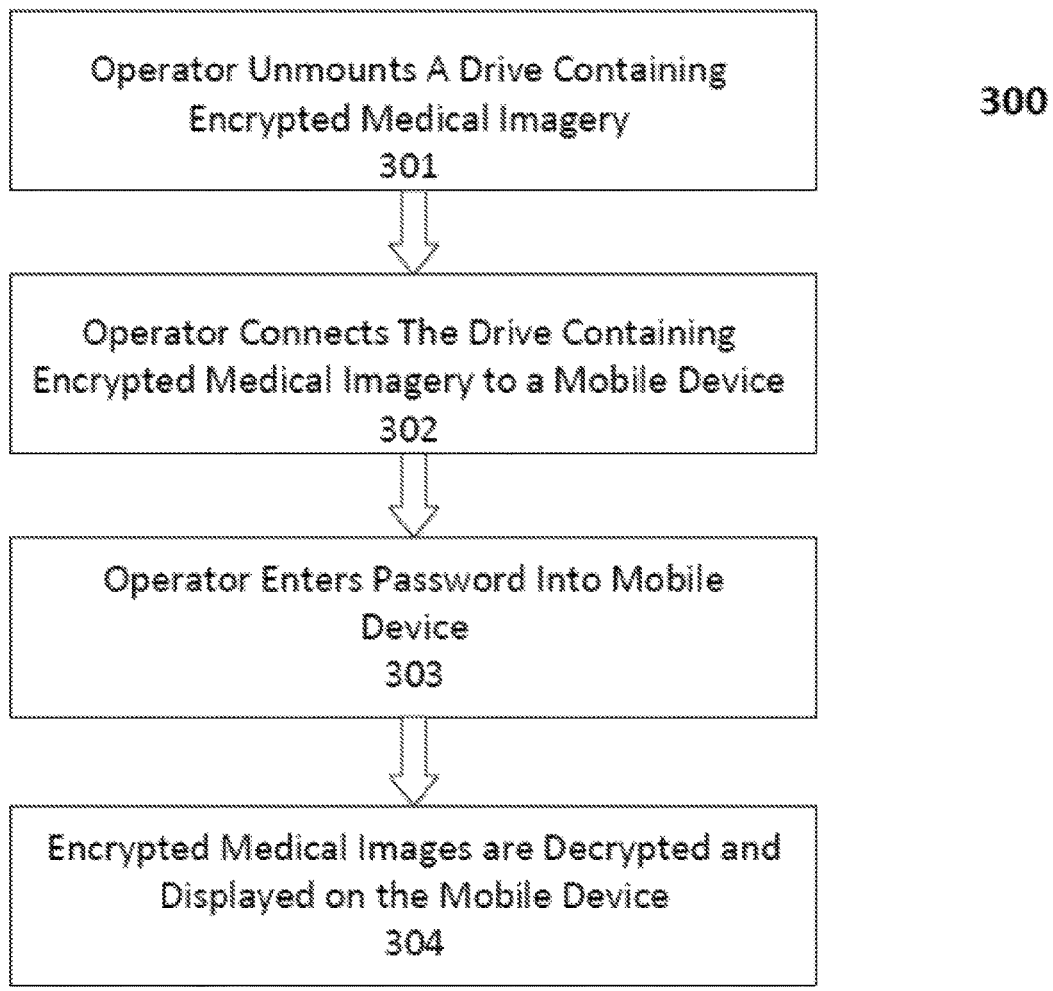
FIG. 3 is a flow chart showing an example process for digital image display according to one embodiment.

FIG. 3 exemplifies one embodiment of a process to show digital images or video to patients. Merely by way of example, the following steps may be used in an embodiment of this process. An operator unmounts a drive that contains encrypted medical imagery 301. In some embodiments this drive may be further secured by a process that conceals the patient's personally identifiable information. Next the operator connects the drive containing encrypted medical imagery to a mobile device 302. In one embodiment the mobile device may be a tablet, cell phone, or laptop computer. The operator then enters a password into the mobile device 303. The password may in some embodiments be an alpha numeric comprising one or more of a string of letters, numbers and/or special characters. The password may also be a biometric reference such as a fingerprint, voice print, facial recognition, or retinal scan. The encrypted medical images are then decrypted and displayed on the mobile device 304. In some embodiments only a certain subsection of the medical images are decrypted.

The drive containing medical imagery of 301 and 302 may be a removable device loaded with digital images, video, and/or audio. In step 302 such removable device may be unmounted in step 301 either by an automatic process or manually by an operator. The removable device may then be physically removed from it's first location and physically loaded unto a mobile device second location such as a mobile device or tablet. The mobile device or tablet may run auto configuration software that detects the loading of a removable device. The auto configurations software may further detect the presence of one or more digital images, videos, and/or audio. The auto configuration software may presents a user with the option of either displaying desired content on the portable second location or transmitting that desired content to a larger display via a cabled connection or wireless technologies as further disclosed herein.

In some embodiments of FIG. 3, additional elements, drivers, sensors, chips, or modules, such as a memory storage device (random-access memory, read-only memory, flash memory, or solid state storage (SSD)), not expressly illustrated in FIG. 3. It is to be noted that all or parts of the steps in FIG. 3 may be concurrently, continuously, periodically, intermittently, repeatedly, or iteratively performed, and the illustrated process in FIG. 3 is only one example embodiment of the features disclosed herein.

Figure 4:
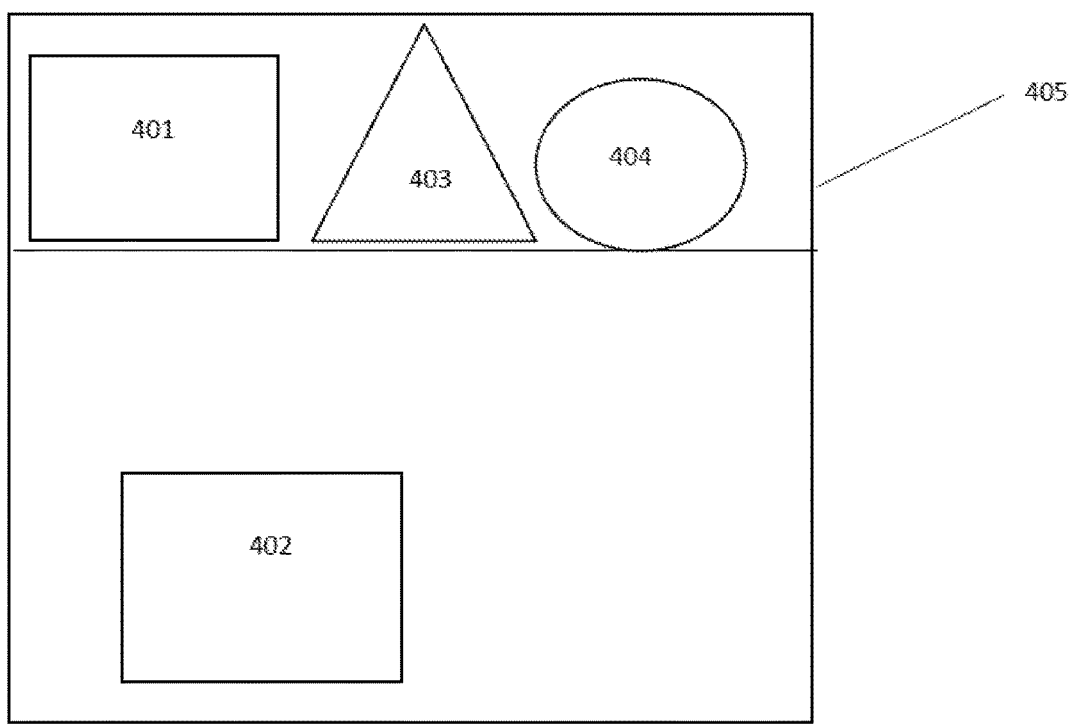
FIG. 4 shows one embodiment of the invention.

FIG. 4 shows one exemplary embodiment of a system that implements the disclosed invention 400 may comprise a specially configured computer 401, a color printer 402, a removable read-write digital memory device 403, a separate voice recognition device 404, a mobile transport device 405 configured to house the specially configured computer 401, the color printer 402, the removable read-write digital memory device 403, and the separate voice recognition device 404. The individual elements of such an embodiment will be discussed in more detail below.

One exemplary specially configured computer 401 of the system that implements the disclosed invention 400 may be configured with a with a built in Quick Sync Video processor or other form of built in graphics processing capable of processing HD content including h.264 encoding. Further the specially configured computer may be configured to accept a with a removable read-write digital memory device 403. The specially configured may additionally be configured to securely encrypt data using hardware acceleration or specially configured encryption software. In some embodiments, such specially configured software may be configured to encrypts one or more segments of data automatically, without any user intervention.

The color printer 402 may be configured to print color photos from the specially configured computer 401. Color printer 402 may be connected to specially configured computer 401 using a wireless encrypted connection. In some embodiments, color printer 402 may be further configured to print both black and white images, color prints, and color photos, where color photos differ from color prints by the use of either glossy print paper and or image resolution defined by dots for inch or a similar mechanism.

The removable read-write digital memory device 403, may be a compact flash card, secure digital card, memory stick, solid state memory (SSD) or removable hard drive. In some embodiments the read-write digital memory device 403 may be configured so that it contains one or more logical partitions for storage. In some embodiments, there may be more than one logical partition with each partition encrypted with a separate key. In other embodiments the data no the removable read-write digital memory device 403 may be encrypted distinct from any encryption that is already formatted onto any logical partition.

The separate voice recognition device 404 may in some embodiments be a physically separate device from the specially configured computer 401. In one embodiment the separate voice recognition device 404 may be an Amazon Echo or Amazon Dot. In another embodiment the separate voice recognition device 404 may be a specially programmed device with a voice recognition library that is optimized for medical terminology. In other embodiments the separate voice recognition device 404 is configured so that is may be trained by an end user to recognize the particular speech patterns of an end user.

A mobile transport device 405 is prepared to transport the specially configured the specially configured computer 401, the color printer 402, the removable read-write digital memory device 403, and the separate voice recognition device 404. In one embodiment the mobile transport device 405 is configured with an uninterruptable power supply to provide power to one or more electronic components. Further network connection equipment including a wired or wireless router, modem, and one or more network switch may also be installed on the mobile transport device 405.

It will be further understood that FIG. 4 illustrates an aspect of a device or system which may perform the image collection and processing as described in relation to FIG. 1, and thus may be one implementation of the user system described herein. The system contains a device, that device being an example of a computing or processing device that may implement at least parts of the various methods described herein. The device may include a processor which controls operation of the device. The processor may also be referred to in some embodiments as a central processing unit (CPU). The processor may comprise or be a component of a processing system implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, graphics processor units (GPUs), or any other suitable entities that can perform calculations or other manipulations of information.

In some embodiments, the processor may be configured to identify and process images received from the image and location database. Processing the images may comprise analyzing the image to identify objects and/or open spaces or regions within the image. In some embodiments, the processor may only analyze pre-processed images.

Memory which may include both read-only memory (ROM) and random access memory (RAM), may provide instructions and data to the processor. A portion of the memory may also include non-volatile random access memory (NVRAM). The processor typically performs logical and arithmetic operations based on program instructions stored within the memory. The instructions in the memory may be executable to implement the methods described herein. The memory may also comprise machine-readable media.

In some embodiments, the memory may temporarily or permanently store received and/or processed images. For example, a high definition medical image and corresponding audio commentary may be stored in the memory such that selection of an point of interest (POI) designated by an operator or the device is associated with a particular image of the memory. In some embodiments, the memory may also comprise memory used while the received images are being processed. For example, a requested image may be stored in the memory in advance of the operator's selection of a point of interest or address associated with the image.

In some embodiments, the memory may temporarily or permanently store received and/or processed high definition video. For example, a high definition video of a selection from a medical procedure and corresponding audio commentary may be stored in the memory such that selection of a point of interest (POI) designated by an operator or the device is associated with a particular image of the memory. In some embodiments, the memory may also comprise memory used while the received the high definition video or audio commentary associated with the POI is being processed. For example, a requested video may be stored in the memory in advance of the operator's selection of a POI or address associated with the video.

The processing system may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described herein. Accordingly, the processing system may include, e.g., hardware, firmware, and software, or any combination therein.

Microphone may include any structure configured to capture audio and generate audio signals. As depicted in FIG. 4, microphone may be centrally located on the system to capture audio and may be configured to capture voice commands from the operator to direct the actions of the system without risking contamination by touching a component that is not sterile. Alternatively, microphone may be worn by the operator or placed in a location where optimal audio capture may be achieved. Microphone may also be configured capture audio which may be transcribed into text utilizing voice to text processing software.

The user interface may be configured to receive input from the user and transmit media. User interface may include an LCD, an LED, a plasma display, or any other type of display. User interface may provide a Graphical User Interface (GUI) presented on the display for user input and data display. User interface may further include a touchscreen, a keyboard, a mouse, or a tracker ball to enable user input. User interface may be configured to receive user-defined settings.

The system may also include a housing that may include a transmitter and/or a receiver to allow transmission and reception of data between the device and a remote location or device. The transmitter and receiver may be combined into a transceiver. An antenna may be attached to the housing and electrically coupled to the transceiver (or individually to the transmitter and the receiver) to allow for communication between the device and external devices. The device may also include (not shown) multiple transmitters, multiple receivers, and/or multiple transceivers.

The transmitter (or transmitter portion of the transceiver) can be configured to wirelessly transmit messages. The processor may process messages and data to be transmitted via the transmitter. The transmitted information may comprise location coordinates or points of interest (user selected or processor identified) that may identify medical high definition images, video, and/or audio requested by the device from the secure image, video and/or audio database. The transmitter may also transmit information generated by the processor or the operator, such as generated boundaries or specifically noted information regarding a specific item noted by an operator (e.g., a particular structure of interest or other medically significant element). Such transmissions by the transmitter may allow generated information to be shared between other users of the system or other operators, medical professionals, patients, medical billing agents, insurance companies, etc. In some embodiments, the high definition video, images, and/or audio may be stored locally such that the transmitter is not involved in communicating user entered address or POI information in a request for a high definition video, image, and/or audio.

The receiver (or the receiver portion of the transceiver) can be configured to wirelessly receive messages. The processor may further process messages and data received via the receiver. In some embodiments, the receiver may receive the images from one of the image location database or the camera (or the centralized system controller or database or another user). Accordingly, the images received may be either processed or unprocessed. When the high definition images and/or video is received are received having been processed, then the high definition images and/or video may be sent directly to the processor for analysis.

The various components of the device may be coupled together by a bus system. The bus system may include a data bus, for example, as well as a power bus, a control signal bus, and a status signal bus in addition to the data bus. Those of skill in the art will appreciate that the components of the device may be coupled together or accept or provide inputs to each other using some other mechanism.

The various components of the system may be coupled together by a computer network system. The computer network may be any type of wired or wireless network that may allow transmitting and receiving data. For example, network may be a nationwide cellular network, a local wireless network (e.g., Bluetooth™ or WiFi, Near Field Communication 'NFC.), or a wired network. Mobile communication devices and/or third party device may also be configured to transmit secure medical data using formats and protocols that comply with HIPPA and other data security protocols as later discussed in detail.

The present disclosed system additionally includes security features not found in any other medical video recording system out in the market. The disclosed separate medical imaging processing system consists of the cart which may contain at least: a computer, mouse, monitor, printer, music system, and equipment used for video recording. In will be understood that all patient medical records are covered strict government policies ensuring patient privacy. One such set of government policies is found in the U.S. Health Information Portability and Privacy Act. (HIPPA) The patient data privacy requirements of this act are one of the driving features for the present disclosure.

In some implementations a medical imaging system is configured with a camera or digital recording device that is configured to send secure video signal to a separate medical imaging processing system in such a way that there is no identifiable patient information. In one embodiment, the digital recording device is a camera that transmits high-definition video. High-definition video may in some implementations have at least 921,600 pixels per image. In other implementations, high-definition video may have more than 3,000,000 pixels per image and in some implementations, high-definition video may have 33,177,600 pixels per image.

It will be readily understood that the most dangerous part of any secure process is the final resting place of the data. In a traditional recording system, the images, data, and patient information a stored on the recording equipment which contains a storage device. If a theft occurs, it is possible that all data in regards to all patient encounters can become compromised. A point of uniqueness in the current disclosure is that all information transmitted by the medical imaging system may be encrypted and secure throughout the process. No patient information is stored in the separate medical imaging processing system. All final resting places of the data reside in secure removable media that can be used in standard computing environments requiring no technical skills or additional complex processes to manipulate and store the data.

If the data from the separate medical imaging processing system, is lost or stolen, the previously mentioned secure storage ensures security compliance due to its encryption. The data stored in the separate medical imaging processing system, once it has been transported, can be manipulated and stored in accordance to local IT policies and procedures. Patient security and compliance is not the responsibility of the location of where the separate medical imaging processing system is located.

In one embodiment a system for recording HIPAA compliant medical imagery may be configured using two separate systems. A first system comprising a separate and independent medical imaging device such as a microscope, an endoscope, or a similar medical imaging tool. The desired medical imaging tool is configured so that a high-definition recording device is able to capture the imagery displayed by the medical imaging tool. The separate and independent medical imaging device is further configured to transmit the high-definition captured imagery to a second separate and independent medical imagery processing system.

The second separate and independent medical imagery processing system may be configured to include a special purpose computer with at least a processor, a hard drive, a random-access memory, and a removable encrypted flash drive. The processor may be configured, using well understood techniques, to process the high-definition imagery that is transmitted from the separate and independent medical imaging device. The processor may be further configured to store the processed data in an encrypted format only on a removable encrypted flash drive that is connected to the second separate and independent medical imagery processing system.

In some embodiments the removable encrypted flash drive that is connected to the second separate and independent medical imagery processing system is encrypted using an algorithm selected from FIPS 140-2 Annex A. The FIPS 140-2 Annex A is a routinely updated list of secure encryption algorithms that can be used to protect sensitive data for uses such as HIPPA compliance. The Advanced Encryption Standard (AES), Triple-DES Encryption Algorithm (TDEA), and Asymmetric Key (DSS-DSA, RSA and ECDSA) are commonly used FIPS 140-2 Annex A algorithms for encrypting data. It will be understood that other similar encryption algorithms, whether or not they are included in the FIPS 140-2 Annex A, may be used as well.

In some embodiment a mobile device such as a tablet, a smart phone, or a laptop computer may be configured to accept the removable encrypted flash drive and decrypt its contents. Access to the encrypted content on the removable encrypted flash drive may require a key. In some embodiments, this key may be a password or a passphrase. In other embodiments, a biometric access key may be provided by using biometric security systems such as a fingerprint recognition device, a facial recognition sensor system, or a voice recognition system. It will be understood that other well-known device authentication systems may be used to provide a key to decrypt the removable encrypted flash drive.

Although a number of separate components are discussed above those of skill in the art will recognize that one or more of the components may be combined or commonly implemented. For example, the processor may be used to implement not only the functionality described above with respect to the processor, but also to implement the functionality described above w the image processor. Further, each of the components disclosed herein may be implemented using a plurality of separate elements.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like. Further, a "channel width" as used herein may encompass or may also be referred to as a bandwidth in certain aspects.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The technology is operational with numerous other general purpose or special purpose computing system environments or configurations. Examples of well-known computing systems, environments, and/or configurations that may be suitable for use with the development include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

A processor may be any conventional general purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

The system may be used in connection with various operating systems such as Linux®, UNIX® or Microsoft Windows®. The system control may be written in any conventional programming language such as C, C++, BASIC, Pascal, or Java, and ran under a conventional operating system. C, C++, BASIC, Pascal, Java, and FORTRAN are industry standard programming languages for which many commercial compilers can be used to create executable code. The system control may also be written using interpreted languages such as Perl, Python or Ruby.

Those of skill will further recognize that the various illustrative logical blocks, modules, circuits, and algorithm steps described in connection with the implementations disclosed herein may be implemented as electronic hardware, software stored on a computer readable medium and executable by a processor, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present development.

The various illustrative logical blocks, modules, and circuits described in connection with the implementations disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microproc an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present development. At the very least, and not as an attempt to limit the application of the doctrine of equivalents to the scope of the claims, each numerical parameter should be construed in light of the number of significant digits and ordinary rounding approaches.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

What is claimed is:

1. A system for recording HIPAA compliant medical imagery comprising:
    a first medical imaging system comprising a medical imaging device;
    the first medical imaging system configured to capture imagery and transmit that imagery as medical files to a second medical imaging system;
    the second medical imaging system comprising:
        a special purpose computer;
        the special purpose computer comprising:
            a first processor, a second processor, a permanently installed hard drive, and a random access memory;
            wherein the first processor is a GPU;
            wherein the second processor is a CPU;
            wherein the permanently installed hard drive is configured such that it stores all instructions necessary for the first processor to process medical files transmitted from the first medical system;
            wherein the permanently installed hard drive is further configured such that it stores all instructions necessary for the second processor to encrypt and store all medical files, as they are created, on a removable drive only; and
            wherein the removable drive is an encrypted removable flash storage drive.

2. The system for recording HIPAA compliant medical imagery of claim 1, wherein the removable encrypted flash drive is encrypted using an algorithm selected from FIPS 140-2 Annex A.

3. The system for recording HIPAA compliant medical imagery claim 2,
    wherein the removable encrypted flash drive is configured such that it can be inserted into a preconfigured slot located in a mobile device;
    the mobile device configured to contain the removable encrypted flash drive without altering the exterior shape of the mobile device.

4. The mobile device of claim 3, wherein the mobile device is configured to decrypt the contents of the removable encrypted flash drive through use of a biometric access key.

5. The system for recording HIPAA compliant medical imagery of claim 1,
    wherein the first medical imaging system is configured to transmit imagery to the medical imagery processing system over a wireless communication network;
    the wireless communication network comprising:

at least one wireless network card installed on the first medical imaging system; at least one wireless network card installed on the medical imagery processing system.

6. The wireless network of claim 4, wherein the wireless network is uses the IEEE 802.1x compliant authentication; and the wireless network is FIPS 140-2 compliant.

7. The system for recording HIPAA compliant medical imagery of claim 1 wherein the first medical imaging system comprises at least one microscope.

8. The system for recording HIPAA compliant medical imagery of claim 1
wherein the first medical imaging system comprises at least one endoscope.

9. The system for recording HIPAA compliant medical imagery of claim 1
wherein the first medical imaging system is configured to accept different medical imagery collection devices.

10. The medical imaging processing system of claim 1, further comprising:
a separate dedicated video processing unit;
the separate dedicated video processing unit configured to have at least one unique processor.

11. The removable encrypted flash drive of claim 1, further comprising:
a plurality of logical partitions;
at least one of the plurality of logical partitions encrypted with an algorithm selected from FIPS 140-2 Annex A.

12. A method of capturing high definition medical imagery comprising:
obtaining medical imagery using a first medical imaging system comprising:
a microscope; and
a high definition camera;
transmitting the obtained medical imagery as from the first medical imaging system to a second medical imaging system;
processing the obtained medical imagery on the medical imagery processing system;
the processing of the obtained medical imagery comprising:
utilizing a special purpose computer;
the special purpose computer comprising:
a first processor, a second processor, a permanently installed permanently installed hard drive, and a random access memory;
wherein the first processor is a GPU;
wherein the second processor is a CPU;
wherein the permanently installed hard drive is configured such that it stores all instructions necessary for the second processor to process imagery transmitted from the first medical system;
wherein the first hard drive is further configured such that it stores all instructions necessary for the second processor to encrypt and store all processed imagery, as the processed imagery is created, on a removable drive only; and
wherein the removable drive is an encrypted removable flash storage drive.

13. The method of capturing high definition surgical imagery of claim 12,
wherein the removable encrypted flash drive is removed from the medical imaging processing system;
the removable encrypted flash drive is inserted into a preconfigured slot located within a mobile device; and
wherein the mobile device is configured to contain the removable encrypted flash drive without altering the exterior shape of the mobile device.

14. The method of capturing high definition medical imagery of claim 12, wherein the second medical imaging processing system further comprises:
a separate dedicated video processing unit.

15. The method capturing high definition medical imagery of claim 12,
wherein the removable encrypted flash drive is encrypted using an algorithm selected from FIPS 140-2 Annex A.

16. The mobile device of claim 12, wherein the mobile device is configured to decrypt the contents of the removable encrypted flash drive through use of a biometric access key.

17. The method capturing high definition medical imagery of claim 12, wherein the medical imaging processing system is configured to be controlled by voice commands; wherein the voice commands are processed by a unique specially configured processor.

18. The method capturing high definition surgical imagery of claim 12, wherein the separate removable read-write encrypted digital memory of claim 1, further comprises:
a plurality of logical partitions;
at least one of the plurality of logical partitions encrypted with an algorithm selected from FIPS 140-2 Annex A.

19. The method capturing high definition surgical imagery of claim 12,
wherein the first medical imaging system and the medical imaging processing system are both connected to the same isolated wireless network.

20. A non-transitory computer-readable medium storing instructions which, when executed, cause one or more processors to perform a method of transferring data from a communication device located on a first medical imaging system to a secure encrypted flash drive, the method comprising:
obtaining medical imagery using a first medical imaging system comprising:
a microscope; and
a high definition camera;
transmitting the obtained medical imagery from the first medical imaging system to a second medical imaging system;
processing the obtained medical imagery on the medical imagery processing system;
the processing of the obtained medical comprising:
utilizing a special purpose computer;
the special purpose computer comprising:
a first processor, a second processor, a permanently installed hard drive, and a random access memory;
wherein the permanently installed hard drive is configured such that it stores all instructions necessary for the second processor to process imagery transmitted from the first medical system;
wherein the permanently installed first hard drive is further configured such that it stores all instructions necessary for the second processor to encrypt and store all processed imagery, as it is created, on a removable drive only; and
wherein the removable drive is an encrypted removable flash storage drive.

* * * * *